US006538158B2

(12) United States Patent
Zechlin et al.

(10) Patent No.: US 6,538,158 B2
(45) Date of Patent: Mar. 25, 2003

(54) PROCESS FOR PREPARING 1,4-DIAMINONAPHTHALENE AND/OR 1,5-DIAMINONAPHTHALENE

(75) Inventors: Joachim Zechlin, Düsseldorf (DE); Lothar Duda, Düsseldorf (DE); Gerhard Wegener, Mettmann (DE); Andreas Hoffmann, Köln (DE); Bodo Temme, League City, TX (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/138,542

(22) Filed: May 3, 2002

(65) Prior Publication Data

US 2002/0198408 A1 Dec. 26, 2002

(30) Foreign Application Priority Data

May 8, 2001 (DE) .......................... 101 22 234

(51) Int. Cl.⁷ ............................ C07C 209/00
(52) U.S. Cl. .................. 564/405; 564/407; 564/347
(58) Field of Search ............... 564/405, 407; 560/347

(56) References Cited

U.S. PATENT DOCUMENTS

| 1,775,360 A | 9/1930 | Williams |
| 2,391,848 A | 12/1945 | Slagh ........................ 260/581 |
| 4,405,527 A | 9/1983 | Wegener et al. ...... 260/453 PH |
| 4,973,758 A | 11/1990 | Behre et al. ............... 564/394 |

FOREIGN PATENT DOCUMENTS

| DE | 45549 | 11/1888 |
| DE | 234912 | 5/1911 |
| DE | 2403656 | 10/1974 |
| JP | 51-133237 | 11/1976 |
| JP | 52-96295 | 8/1977 |
| JP | 6-346050 | 12/1994 |
| JP | 7-22670 | 1/1995 |
| JP | 07278066 | * 10/1995 |

OTHER PUBLICATIONS

Salkind, J.; Stetzuro, Z. : "Umlagerungen der Dibromnaphthaline durch Aluminiumchlorid".
Chemische Berichte, Bd. 64,—1931 Seite 953–954 XP001097475 Seite 953.
Rev. Farm. Bioquim. Univ. Sao Paulo, Jan./Dec. 1977, 15 (1/2), pp. 19–25, Andrejus Korolkovas, Guang–Nan Yang and Eliane Manfrinato, "Sintese De Esquistossomicidas Potenciais Derivados Da 1,4–Naftilendiamina".
J. Parkt. Chem., 156, (month unavailable) 1940, pp. 315–316, Von H. Goldhahn, "Darstellung des 4–Nitronaphthylamin–1".
Annalen Der Chemie, vol. 562, (month unavailable) 1949, pp. 1–14, Von K. Bodendorf, K.J. Krüger und F. Zernial, "Eine Gruppe neuer cocainähnlicher Lokalanästhetika".

* cited by examiner

*Primary Examiner*—Samuel Barts
(74) *Attorney, Agent, or Firm*—Joseph C. Gil; Lyndanne M. Whalen

(57) ABSTRACT

1,4-diaminonaphthalene and/or 1,5-diaminonaphthalene are produced by (a) reacting naphthalene with a halogen, (b) optionally, separating 1,4-dihalogen naphthalene or 1,5-dihalogen naphthalene from the mixture from step (a), and (c) reacting the mixture from step (a) or the 1,4-dihalogen naphthalene or the 1,5-dihalogen naphthalene from step (b) with ammonia and/or an organic amine in the presence of a catalyst.

19 Claims, No Drawings

PROCESS FOR PREPARING 1,4-DIAMINONAPHTHALENE AND/OR 1,5-DIAMINONAPHTHALENE

BACKGROUND OF THE INVENTION

The present invention relates to a process for preparing 1,4-diaminonaphthalene and/or 1,5-diaminonaphthalene from naphthalene.

1,4-diisocyanatonaphthalene was mentioned for the first time in the literature as a starting material for polyurethanes in Ann. Chem. 562, 6 (1949). Due to the lack of a cost-effective manufacturing process for 1,4-diaminonaphthalene and hence for 1,4-diisocyanatonapththalene, only a few areas of application for 1,4-diisocyanatonaphthalene are described in the literature. Examples of such areas of application are the preparation of polyurethane-based adhesives or fiber additives, which are disclosed in JP-A2-52096295 and DE-A1-2403656.

An isocyanate component used for the preparation of naphthalene-based polyurethane according to the prior art is mainly 1,5-diisocyanatonaphthalene, which is used in the preparation of polyurethane elastomers.

1,5-diisocyanatonaphthalene is prepared industrially by the phosgenation of the corresponding diamine 1,5-diaminonaphthalene. In accordance with the prior art, 1,5-diaminonaphthalene is prepared via the sulfonation of naphthalene and the subsequent substitution of the sulfonic acid groups with amino groups (DE-C1-3840618).

1,4-diaminonaphthalene, on the other hand, is reacted with 1,4-naphthalene diisocyanate for the synthesis of polyamides, polyimides and polyimines, and also for the preparation of conductive or electro-luminescent polymer materials, as described, for example, in the patent specifications JP-A2-06346050 and JP-A2-07022670.

Preparation of 1,4-diaminonaphthalene in accordance with the prior art is currently limited to preparation by azocoupling starting with 1-naphthylamine (JP-A2-51133237, Rev. Farm. Bioquim. Univ. Sao Paolo (1977), 15 (1–2), 19–25) and via the reaction of hydroxylamine with nitronaphthalene in strongly alkaline medium to form 1-nitro-4-aminonaphthalene (J. prakt. Chem. 156, 315 (1940), Chem. Ber., 22 (1899) 1374). These processes represent multi-stage syntheses with high production costs and low yields in addition to cost-intensive raw materials.

Polyurethanes based on 1,4-diisocyanatonaphthalene and 1,5-diisocyanatonaphthalene possess advantageous properties, so that a practicable synthesis routes for the preparation of 1,4-diaminonaphthalene and 1,5-diaminonaphthalene and their corresponding isocyanates are required.

SUMMARY OF THE INVENTION

The object of the present invention is to provide a simple process for the preparation of 1,4-diaminonaphthalene and/or 1,5-diaminonaphthalene.

This and other objects which will be readily apparent to one skilled in the art are accomplished by reacting naphthalene with a halogen and reacting the halogenated naphthalene with ammonia and/or an organic amine, optionally, in the presence of a catalyst.

DETAILED DESCRIPTION OF THE INVENTION

The present invention relates to a process for preparing 1,4-diaminonaphthalene and/or 1,5-diaminonaphthalene by a) reacting naphthalene with a halogen, b) optionally, separating 1,4-dihalogen naphthalene and/or 1,5-dihalogen naphthalene from the mixture from step a), c) re acting the mixture from step a) or the 1,4-dihalogen naphthalene and/or the 1,5-dihalogen naphthalene from step b) with ammonia and/or an organic amine in the presence of a catalyst.

The selective dihalogenation of naphthalene can take place in the absence of a catalyst or it may be catalyzed but it is preferably catalyzed.

If a catalyst is used, suitable catalysts for the dihalogenation reaction include iodine, tin, elements of Groups 8, 10, 12 and 13 of the Periodic Table (nomenclature to I.U.P.A.C 1985), mineral acid salts and oxides of the elements of Groups 8, 9, 10, 12, 13, 14 and 15 of the Periodic Table (nomenclature to I.U.P.A.C 1985) and mineral acids.

Preferably, iodine, iron, tin, zinc, aluminum, nickel, halides or oxides of iron, nickel, aluminum, antimony, arsenic, tin, zinc, boron or phosphoric acid are used.

Suitable halogens include chlorine, bromine and mixtures thereof.

In principle, any solvent which is able to dissolve naphthalene and is not halogenated to a significant extent under the prevailing conditions may be used in the process of the present invention. Dichloromethane, trichloromethane, tribromomethane, tetrachloromethane, tetrabromo-methane, chlorobenzene, dichlorobenzenes and trichlorobenzenes are preferred. Most preferred is trichloromethane.

The procedure adopted for the dihalogenation is preferably such that the halogen, preferably bromine, is introduced into a mixture of naphthalene, solvent and catalyst at an absolute pressure in the range of from about 0.5 to about 10 bar, preferably from 1 bar to 2 bar, most preferably from 1 bar to 1.2 bar, and at a temperature in the range of from 0° C. to 150° C., preferably from 10° C. to 70° C., most preferably from 20 to 30° C. The naphthalene concentration during the halogenation is preferably in the range of from 5 to 70 wt %, most preferably from 25 to 50 wt %, based on the weight of the solvent.

During the dihalogenation, a mixture containing 1,4-dihalogen naphthalene and 1,5-dihalogen naphthalene is obtained. Prior to amination, the mixture may be purified. The 1,4-dihalogen naphthalene and/or the 1,5-dihalogen naphthalene can also, however, be separated out of the mixture. The 1,4-dihalogen naphthalene or the 1,5-dihalogen naphthalene can be aminated free from isomers in this way.

The separation of the 1,4-dihalogen naphthalene and/or the 1,5-dihalogen naphthalene out of the mixture can be accomplished by taking advantage of the large melting point difference of these isomers, for example, by crystallization.

The halogen-amine substitution is performed in the presence of a catalyst. Suitable catalysts include any of the metals of Groups 8, 9, 10 and 11 of the Periodic Table (nomenclature to I.U.P.A.C 1985) and oxides, acetates and mineral acid salts of metals of Groups 8, 9, 10 and 11 of the Periodic Table (nomenclature to I.U.P.A.C 1985).

The metal catalyst can be in the form of granules, chips, powder or fixed to a support, for example on aluminum oxide, silicon oxide or titanium oxide, or in any other solid form. The chlorides, acetates and oxides can be used, for example, in the form of pellets or as powder or fixed to a support such as aluminum, silicon or titanium oxide.

Preferably nickel, copper, cobalt or iron metal, halides of iron, nickel, copper, cobalt, oxides of iron, nickel, copper, cobalt, acetates of iron, nickel, copper, cobalt are used.

In principle, any solvent which is able to dissolve dihalogen naphthalene and is inert under the prevailing conditions may be used in the process of the present invention. Preferably, water, methanol, ethanol, N,N-dimethyl acetamide, n-propanol, n-butanol, acetonitrile, benzonitrile, dioxan or dioxan/water mixtures or inert solvents which are immiscible with water such as toluene, xylene or aliphatic or cycloaliphatic hydrocarbons of the $C_6$–$C_{12}$ fraction are used. The use of liquid ammonia as a reaction medium without further solvent addition is also suitable for the amination reaction of the dihalogen naphthalene.

Ammonia as well as any primary and/or secondary amines such as monoalkyl amines, monoacyl amines or dialkyl amines are suitable as amination agents. Ammonia is preferably used.

The yield of the halogen-amine substitution reaction in terms of diamino-naphthalene can be raised considerably if the hydrohalic acid formed, during the reaction is neutralized with a base. Suitable bases include carbonates and hydroxides of Groups 1 and 2 of the Periodic Table (nomenclature to I.U.P.A.C. 1985). Preferably, sodium, potassium, calcium or magnesium carbonate or hydrogencarbonate or sodium, potassium, calcium or magnesium hydroxide or mixtures or mixed crystals thereof are used. The addition of cesium, rubidium or barium chloride, cesium, rubidium or barium sulfate improves the yield-increasing effect of the base. Cesium chloride or cesium sulfate is preferably used.

The halogen-amine substitution is carried out at temperatures in the range of from 0° C. to 200° C., preferably from 100 to 180° C., most preferably from 120 to 160° C. and at a pressure of from 1 to 200 bar, preferably from 10 to 150 bar, most preferably from 20 to 120 bar. The concentration of 1,4- and 1,5-dihalogen naphthalene is preferably in the range of from 5 to 70 wt %, most preferably from 30 to 50 wt %, based on the weight of solvent or ammonia in the case of a solvent-free reaction.

After the amination, a purification step or separation step can be carried out and the desired product removed from the reaction mixture. Suitable separation methods include distillation and crystallization.

The proportion of 1,5-dihalogen naphthalene in the mixture of 1,4-dihalogen naphthalene and 1,5-dihalogen naphthalene is generally in the range of from 1 to 50 wt %, preferably from 5 to 40 wt %, most preferably from 10 to 30 wt %. The isomer ratio is determined by the halogenation as a function of the choice of catalyst and the reaction temperature and remains substantially unaltered during the subsequent amination.

The invention also provides a process for preparing mixtures containing 1,4-diisocyanatonaphthalene and 1,5-diisocyanatonaphthalene by
a) reacting naphthalene with a halogen,
b) reacting the mixture from step a) with ammonia in the presence of a catalyst, and
c) phosgenating the mixture from step b).

The present invention also provides a process for preparing 1,4-diisocyanatonaphthalene by
a) reacting naphthalene with a halogen,
b) reacting the 1,4-dihalogen naphthalene from step a) with ammonia in the presence of a catalyst, and
c) phosgenating the 1,4-diaminonaphthalene from step b), in which the 1,5 isomer is separated from the isomer mixture after one of steps a), b) or c).

The invention also provides a process for preparing 1,5-diisocyanatonaphthalene by
a) reacting naphthalene with a halogen,
b) reacting the 1,5-dihalogen naphthalene from step a) with ammonia in the presence of a catalyst, and
c) phosgenating the 1,5-diaminonaphthalene from step b), in which the 1,4 isomer is separated from the isomer mixture after one of steps a), b) or c).

The amines prepared by the process according to the invention can then be phosgenated by any of the known methods to produce the corresponding isocyanate. The resultant isocyanates may be used to produce polyurethanes (e.g. JP-A2-50012062). After phosgenation, a purification step or separation step can be carried out and the desired product, preferably 1,4-diisocyanatonaphthalene, may be removed from the reaction mixture. Suitable separation techniques include distillation and crystallization.

The optionally desired separation of the 1,4 isomer and the 1,5 isomer can also take place after the dihalogenation and/or after the halogen-amine substitution and/or after the phosgenation.

Having thus described the invention in detail, the following Examples are given as being illustrative thereof. All parts and percentages given in these Examples are parts by weight and percentages by weight, unless otherwise indicated.

EXAMPLES

Example 1

Selective Naphthalene Bromination in Tetrachloromethane 32 g of naphthalene were mixed for 30 min with 88 g of bromine with stirring in a 500 ml glass flask together with 2.5 g of iodine as a solution in 170 ml of tetrachloromethane at room temperature by means of a dropping funnel. After complete addition of bromine, stirring was continued for an additional hour at room temperature, then excess bromine and iodine were reduced by shaking with 100 ml of a 10% aqueous sodium sulfite solution. After separation of the aqueous phase, the product solution in tetrachloromethane was analyzed by gas chromatography.

The selectivity determined in terms of 1,4-/1,5-diaminonaphthalene was 97.25% (GC). The ratio of 1,4-diaminonaphthalene to 1,5-diamino-naphthalene was 78.86%:18.39% (GC).

The analyses required for the selectivity determination were performed with a gas chromatograph (GC).

Example 2

Selective Naphthalene Bromination in Trichloromethane 128 g of naphthalene were mixed slowly for a period of one hour with 352 g of bromine with stirring in a 2000 ml glass flask together with 10 g of iodine as a solution in 700 ml of trichloromethane at room temperature. When the addition of bromine had taken place, stirring was carried out for an hour and the remaining bromine and iodine were then shaken out with 500 ml of a 10% aqueous sodium sulfite solution. After separation of the aqueous phase and subsequent distilling off of the solvent, the product remained.

281.44 g of solid were obtained (=98.4 mol. % of theoretical, based on the weight of the dibromonaphthalene used). The purity of the product determined by gas chromatography was 97.63% of 1,4-/1,5-diaminonaphthalene mixture. The ratio of 1,4-diaminonaphthalene to 1,5-diaminonaphthalene was 85.34%:12.29% (GC).

The total yield of 1,4- and 1,5-diaminonaphthalene mixture was determined as 96.1% (GC).

Example 3 a) Joint Separation of Solvent and Iodine Catalyst (Solvent: Tetrachloromethane)

50 g of a 1,4-/1,5-dibromonaphthalene mixture prepared in accordance with Example 2 were mixed in a glass flask with 150 ml of tetrachloromethane and 1.1 g of iodine. During hot-air heating at 140° C., the solvent was separated by distillation together with a major part of the iodine at standard pressure via a Vigreux column. The remaining iodine was separated by distillation with 200° C. hot air at an absolute pressure of 10 mbar with the use of nitrogen as stripping gas. A colorless solid product was obtained when the separation was completed.

b) Joint Separation of Solvent and Iodine Catalyst (Solvent: Tribromomethane)

50 g of a 1,4-/1,5-dibromonaphthalene mixture prepared in accordance with Example 2 were mixed in a glass flask with 150 ml of tetrabromomethane and 1.1 g of iodine. The solvent was separated by distillation together with the iodine at an absolute pressure of 50 mbar and a bottom temperature of 100° C. A colorless solid product was obtained when the separation of the solvent was completed.

Example 4

Bromo/amino Substitution on 1,4-/1,5-Dibromonaphthalene Mixture with $CuCl_2$ (Anhydrous)

50 g of a 1,4-/1,5-dibromonaphthalene mixture prepared in accordance with Example 2 were placed together with 10 g of $CuCl_2$ (anhydrous) and 250 ml of 25% ammonia liquor in a 500 ml pressure autoclave. An additional 100 g of ammonia were introduced and the contents were then heated to 150° C. The pressure rose to 38 bar.

After a reaction time of 6 h, the reaction was terminated by cooling and blowing off the remaining ammonia. The selectivity of the reaction in terms of the 1,4-/1,5-diaminonaphthalene mixture, determined by gas chromatography, was 61.50% (GC).

Example 5

Bromo/amino Substitution on 1,4-/1,5-Dibromonaphthalene Mixture with CuCl (Anhydrous)

40 g of a 1,4-/1,5-dibromonaphthalene mixture prepared according to Example 2 were placed together with 6 g of CuCl (anhydrous) and 250 ml of 25% ammonia liquor in a 500 ml pressure autoclave. An additional 100 g of ammonia were introduced and the reactor contents were then heated to 150° C. with stirring. The pressure rose to 41 bar.

After a reaction time of 6 h, the reaction was terminated by cooling and blowing off the remaining ammonia. The selectivity of the reaction in terms of the 1,4-/1,5-diaminonaphthalene mixture, determined by gas chromatography, was 61.32% (GC).

Example 6

Phosgenation of 1,4-Diaminonaphthalene to 1,4-Diisocyanatonaphthalene

To a solution of 250 g of 1,4-NDA in 2 l of 96% ethanol was added 300 ml of 37% hydrochloric acid. The precipitated 1,4-diaminonaphthalene dihydrochloride was filtered off, scrubbed with a small amount of 96% ethanol and dried 323 g of 1,4-diaminonaphthalene dihydrochloride were obtained.

188.9 g of 1,4-diaminonaphthalene dihydrochloride with 99.3% purity were suspended in a 10 l glass flask in 6720 ml of monochlorobenzene. After azeotropic dehydration, with the distilling off of 400 ml of monochlorobenzene, phosgene was introduced in an amount of 260 g/h with stirring at a temperature of 80° C. for 1 h via a glass tube. Further phosgenation was then carried out with the same added amount of phosgene for approximately 12 h with stirring at a temperature of 100° C. The suspension first obtained was thus clarified.

After 12 h of dephosgenation by the injection of nitrogen with stirring at room temperature, the monochlorobenzene was separated by distillation and the crude product was pre-distilled at a hot air temperature of approximately 260° C. and a vacuum of <0.1 mbar. The amount of crude distillate amounted to 156 g (=90.9% of theoretical, referred to the 1,4-diaminonaphthalene used).

After precision distillation of the crude distillate via a 50 cm Vigreux column, 141 g of 1,4-diisocyanatonaphthalene with a purity of 99.5% (GC) were obtained.

Example 7

Bromo/amino Substitution on 1,4-/1,5-Dibromonaphthalene Mixture with Copper Acetate with Addition of an Additional Base 30 g of a 1,4-/1,5-dibromonaphthalene mixture prepared according to Example 2 were placed together with 9 g of $Cu(CH_3COO)_2.H_2O$, 14.5 g of $K_2CO_3$, 3.6 g of CsCl and 150 ml of 25% ammonia liquor in a 500 ml pressure autoclave. An additional 150 g of ammonia were introduced and the reactor contents were then heated to 120° C. with stirring. The pressure rose to 39 bar.

After a reaction time of 20 h, the reaction was terminated by cooling and blowing off the remaining ammonia. The selectivity of the reaction in terms of the 1,4-/1,5-diaminonaphthalene mixture, determined by gas chromatography, was 79.48% (GC).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of 1,4-diaminonaphthalene and/or 1,5-diamino-naphthalene comprising:
   a) reacting naphthalene with a halogen,
   b) optionally, separating 1,4-dihalogen naphthalene and/or 1,5-dihalogen naphthalene from the mixture from step a),
   c) reacting the mixture from step a) or the 1,4-dihalogen naphthalene or the 1,5-dihalogen naphthalene from step b) with ammonia or an amine in the presence of a catalyst.

2. The process of claim 1 in which bromine and/or chlorine is used in step a).

3. The process of claim 2 in which step a) is carried out in the presence of a catalyst selected from the group consisting of iodine, tin, elements of Groups 8, 10, 12 and 13 of the Periodic Table, mineral acid salts and oxides of elements of Groups 8, 9, 10, 12, 13, 14 and 15 of the Periodic Table and mineral acids.

4. The process of claim 3 in which iron, zinc, aluminum or nickel metal, a halide of iron, nickel, aluminum, antimony, arsenic, tin, zinc or boron , an oxide of iron, nickel, aluminum, antimony, arsenic, tin, zinc or boron or concentrated phosphoric acid is used as the catalyst in step a).

5. The process of claim 1 in which step a) is carried out in the presence of a catalyst selected from the group consisting of iodine, tin, elements of Groups 8, 10, 12 and 13 of the Periodic Table, mineral acid salts and oxides of elements of Groups 8, 9, 10, 12, 13, 14 and 15 of the Periodic Table and mineral acids.

6. The process of claim 5 in which iron, zinc, aluminum or nickel metal, a halide of iron, nickel, aluminum, antimony, arsenic, tin, zinc or boron, an oxide of iron, nickel, aluminum, antimony, arsenic, tin, zinc or boron or concentrated phosphoric acid is used as the catalyst in step a).

7. The process of claim 6 in which step c) is carried out in the presence of a catalyst selected from the group consisting of metals of Groups 8, 9, 10 and 11 of the Periodic Table and oxides, acetates and mineral acid salts of metals of Groups 8, 9, 10 and 11 of the Periodic Table.

8. The process of claim 7 in which the catalyst employed in step c) is nickel, copper, cobalt or iron metal, a halide of nickel, copper, cobalt or iron or an oxide of iron, nickel, copper or cobalt.

9. The process of claim 5 in which step c) is carried out in the presence of a catalyst selected from the group consisting of metals of Groups 8, 9, 10 and 11 of the Periodic Table and oxides, acetates and mineral acid salts of metals of Groups 8, 9, 10 and 11 of the Periodic Table.

10. The process of claim 9 in which the catalyst employed in step c) is nickel, copper, cobalt or iron metal, a halide of nickel, copper, cobalt or iron or an oxide of iron, nickel, copper or cobalt.

11. The process of claim 1 in which step a) is carried out in the presence of a catalyst selected from the group consisting of iron, zinc, aluminum or nickel metal, halides of iron, nickel, aluminum, antimony, arsenic, tin, zinc or boron, oxides of iron, nickel, aluminum, antimony, arsenic, tin, zinc or boron or concentrated phosphoric acid.

12. The process of claim 1 in which step c) is carried out in the presence of a catalyst selected from the group consisting of metals of Groups 8, 9, 10 and 11 of the Periodic Table, oxides of metals of Groups 8, 9, 10 and 11 of the Period Table, acetates of metals of Groups 8, 9, 10 and 11 of the Periodic Table and mineral acid salts of metals of Groups 8, 9, 10 and 11 of the Periodic Table.

13. The process of claim 1 in which step c) is carried out in the presence of a catalyst selected from the group consisting of nickel, copper, cobalt or iron metal, halides of iron, nickel, copper or cobalt and oxides of iron, nickel, copper or cobalt.

14. The process of claim 1 in which step c) is carried out in the presence of a base.

15. The process of claim 7 in which step c) is carried out in the presence of a base.

16. The process of claim 10 in which step c) is carried out in the presence of a base.

17. A process for the production of a mixture containing 1,4-diisocyanatonaphthalene and 1,5-diisocyanatonaphthalene comprising:
   a) reacting naphthalene with a halogen,
   b) reacting the mixture from step a) with ammonia in the presence of a catalyst, and
   c) phosgenating the mixture from step b).

18. A process for the production of 1,4-diisocyanatonaphthalene comprising:
   a) reacting naphthalene with a halogen to produce 1,4-dihalogen naphthalene,
   b) reacting the 1,4-dihalogen naphthalene from step a) with ammonia in the presence of a catalyst to produce 1,4-diaminonaphthalene, and
   c) phosgenating the 1,4-diaminonaphthalene from step b), in which any 1,5-disubstituted naphthalene is separated from the reaction mixture after one of steps a), b) or c).

19. A process for the production of 1,5-diisocyanatonaphthalene, comprising:
   a) reacting naphthalene with a halogen to produce 1,5-dihalogen naphthalene,
   b) reacting the 1,5-dihalogen naphthalene from step a) with ammonia in the presence of a catalyst to produce 1,5-diaminonaphthalene, and
   c) phosgenating the 1,5-diaminonaphthalene from step b), in which any 1,4-disubstituted naphthalene is separated from the reaction mixture after one of steps a), b) or c).

* * * * *